(12) United States Patent
Baril et al.

(10) Patent No.: US 11,426,151 B2
(45) Date of Patent: Aug. 30, 2022

(54) BAG CLOSURE FOR SPECIMEN RETRIEVAL DEVICE

(71) Applicant: COVIDIEN LP, Mansfield, MA (US)

(72) Inventors: Jacob C. Baril, Norwalk, CT (US); Saumya Banerjee, Hamden, CT (US); Matthew A. Dinino, Newington, CT (US); George S. Matta, Plainville, MA (US)

(73) Assignee: COVIDIEN LP, Mansfield, MA (US)

( * ) Notice: Subject to any disclaimer, the term of this patent is extended or adjusted under 35 U.S.C. 154(b) by 592 days.

(21) Appl. No.: 16/430,722

(22) Filed: Jun. 4, 2019

(65) Prior Publication Data

US 2020/0383669 A1 Dec. 10, 2020

(51) Int. Cl.
*A61B 17/00* (2006.01)
*A61B 10/00* (2006.01)

(52) U.S. Cl.
CPC .... *A61B 17/00234* (2013.01); *A61B 10/0096* (2013.01); *A61B 2017/00287* (2013.01)

(58) Field of Classification Search
CPC ............ A61B 17/00234; A61B 17/221; A61B 17/3421; A61B 2017/00287; A61B 2017/00477
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |

(Continued)

FOREIGN PATENT DOCUMENTS

| | | |
|---|---|---|
| DE | 3542667 A1 | 6/1986 |
| DE | 8435489 U1 | 8/1986 |

(Continued)

OTHER PUBLICATIONS

European Search Report EP 12191639.9 dated Feb. 20, 2013.

(Continued)

*Primary Examiner* — Mohamed G Gabr
(74) *Attorney, Agent, or Firm* — Carter, DeLuca & Farrell LLP

(57) ABSTRACT

A specimen retrieval device includes a bag having a closed bottom end portion and an open top end portion. The specimen retrieval device includes a cinch mechanism coupled to the open top end portion. The cinch mechanism includes a flexible band secured to the bag and a cinch coupled to the flexible band. The flexible band is movable relative to the cinch to reduce or enlarge a diameter of the open top end portion of the bag. The cinch is selectively engagable with the flexible band to fix the diameter of the open top end portion of the bag.

19 Claims, 2 Drawing Sheets

(56) References Cited

U.S. PATENT DOCUMENTS

| | | |
|---|---|---|
| 4,991,593 A * | 2/1991 | LeVahn ............... A01N 1/02 |
| | | 128/853 |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinsk et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinsk |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |

(56) References Cited

U.S. PATENT DOCUMENTS

| | | | |
|---|---|---|---|
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0256425 A1 | 11/2005 | Prusiner |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1* | 3/2007 | Zhou ..................... A61B 10/00 604/327 |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0255597 A1 | 10/2008 | Pravong et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0184536 A1 | 7/2013 | Shibley et al. |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2017/0049427 A1 | 2/2017 | Do et al. |
| 2017/0215904 A1 | 8/2017 | Wassef et al. |
| 2017/0224321 A1 | 8/2017 | Kessler et al. |
| 2017/0325798 A1 | 11/2017 | Prior |

FOREIGN PATENT DOCUMENTS

| | | | |
|---|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2014134285 A1 | 9/2014 |
| WO | 2015134888 A1 | 9/2015 |
| WO | 2017189442 A1 | 11/2017 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.

(56) References Cited

OTHER PUBLICATIONS

International Search Report issued in Appl. No. PCT/US2018/058609 dated Feb. 22, 2019.

* cited by examiner

BAG CLOSURE FOR SPECIMEN RETRIEVAL DEVICE

BACKGROUND

Specimen retrieval devices are commonly used during surgical procedures to collect and remove tissue specimens from a patient. Typically, during a surgical procedure in which tissue is transected, e.g., a hysterectomy procedure, a specimen retrieval device including a tissue collection bag is positioned to receive the tissue specimen once the tissue is transected. In some procedures, a grasper may be used to transfer the transected tissue specimen into the bag. Alternately, the bag may be positioned in relation to the tissue specimen to allow the tissue specimen to fall into the bag.

SUMMARY

The disclosure generally relates to specimen retrieval devices with tissue collection bags that are adjustable with cinching mechanisms having a flexible band and a cinch to selectively open and close the tissue collection bags.

In aspects of the disclosure, a specimen retrieval device includes a bag having a closed bottom end portion and an open top end portion. The specimen retrieval device includes a cinch mechanism coupled to the open top end portion. The cinch mechanism includes a flexible band secured to the bag and a cinch coupled to the flexible band. The flexible band is movable relative to the cinch to reduce or enlarge a diameter of the open top end portion of the bag. The cinch is selectively engagable with the flexible band to fix the diameter of the open top end portion of the bag.

In embodiments, the cinch may include a base portion and an arm portion that is pivotally coupled to the base portion between an open position and a closed position. The arm portion may be biased toward the closed position. The arm portion may include a detent that contacts the flexible band. The flexible band may define one or more apertures. The detent may be receivable within the one or more apertures to prevent the flexible band from moving relative to the cinch.

In some embodiments, the flexible band includes a first end portion that is fixedly secured to the cinch and a second end portion that is movable relative to the cinch. The second end portion may extend to a free end. The free end may include a hook configuration that prevents the free end from passing through the cinch.

In embodiments, the flexible band may include shape memory material. The shape memory material may be Nitinol.

According to yet another aspect of the disclosure, a cinch mechanism for a specimen retrieval device includes a flexible band and a cinch. The cinch is coupled to the flexible band. The flexible band is movable relative to the cinch in a first direction to reduce a diameter of a bag of the specimen retrieval device, and in a second direction to enlarge the diameter of the bag. The cinch is selectively engagable with the flexible band to prevent the flexible band from moving relative to the cinch.

In one aspect, this disclosure is directed to method of enabling a diameter of tissue collection bag of a specimen retrieval device to be selectively changed. The method includes positioning an arm portion of a cinch to pivot relative to a base portion of the cinch so that a flexible band is selectively movable relative to the cinch, positioning the flexible band to selectively move in a first direction relative to the cinch to enlarge a diameter of the tissue collection bag or in second direction relative to the cinch to reduce the diameter of the tissue collection bag, and positioning the arm portion to pivot relative to the base portion to secure the flexible band relative to the cinch and fix the diameter of the tissue collection bag.

The details of one or more aspects of the disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
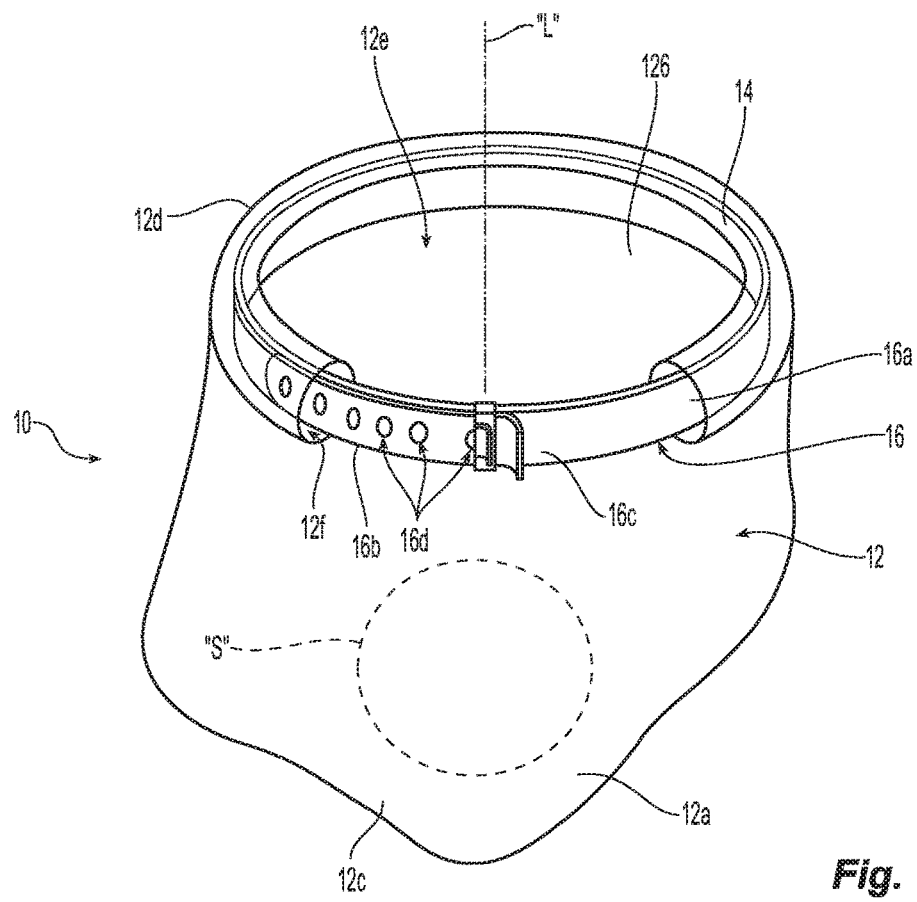
FIG. 1 is a perspective view of a specimen retrieval device shown in an uncinched position in accordance with the principles of this disclosure.

Embodiments of the disclosed specimen retrieval devices are described in detail with reference to the drawings, in which like reference numerals designate identical or corresponding elements in each of the several views. As commonly known, the term "clinician" refers to a doctor (e.g., a surgeon), a nurse, or any other care provider and may include support personnel. In the following description, well-known functions or constructions are not described in detail to avoid obscuring this disclosure in unnecessary detail.

In general, this disclosure describes specimen retrieval devices configured to collect and retain tissue specimens.

With reference to FIG. 1, a specimen retrieval device 10 defines a central longitudinal axis "L" and includes a tissue collection bag 12 and a cinch mechanism 14 coupled to bag 12. Bag 12 includes an outer surface 12a and an inner surface 12b. Bag 12 further includes a bottom end portion 12c that is closed and a top end portion 12d that is open and selectively closable by cinch mechanism 14. In particular, top end portion 12d of bag 12 defines an opening 12e configured to receive a specimen "S" therethrough so that the specimen "S" can be supported in the bottom end portion 12c of bag 12. Bag 12 further defines a cinch channel 12f that supports cinch mechanism 14 therein.

Referring to FIGS. 1-4, cinch mechanism 14 of specimen retrieval device 10 includes a flexible band 16, which may be formed of any suitable material such a shape memory material like Nitinol. Although illustrated with a rectangular configuration, flexible band 16 may include any suitable configuration. Flexible band 16 includes a first end portion 16a that is fixedly secured to a cinch 18 and a second end portion 16b that is selectively movable relative to cinch 18. Second end portion 16b of flexible band 16 extends to a free end 16c. Free end 16c may have a hooked configuration to prevent free end 16c of flexible band 16 from passing through cinch 18. Flexible band 16 defines a plurality of apertures 16d positioned at spaced-apart (e.g., lengthwise) locations along a length of flexible band 16. Each aperture of apertures 16d is configured to correspond to a different diameter of opening 12e of bag 12. Apertures 16d may be provided in flexible band 16 using any suitable manufacturing technique such as stamping, cutting, or the like.

Figure 4:
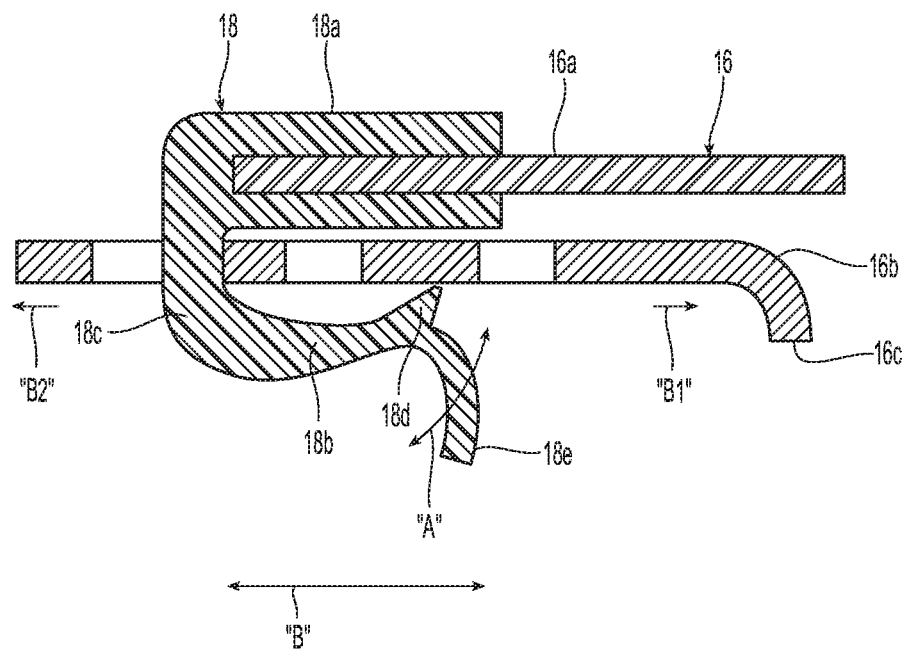
FIG. 4 is a view of the cinch mechanism of FIG. 3 in an unlocked position.

Cinch 18 of cinch mechanism 14 may be formed of any suitable material such as plastic. Cinch 18 includes a base portion 18a to which first end portion 16a of flexible band 16 is fixedly secured. Cinch 18, which may be an integral and/or monolithically formed structure, includes an arm portion 18b that extends from base portion 18a and is flexibly movable relative to base portion 18a about a pivot 18c, as indicated by arrow "A," between a closed position (FIG. 3) and an open position (FIG. 4). Arm portion 18b of cinch 18 may be biased toward the closed position. Arm portion 18b further includes a detent 18d that is selectively receivable within apertures 16d (e.g., one at time) of flexible band 16 when arm portion 18b is disposed in the close position thereof. Arm portion 18b of cinch 18 also extends to a release tab 18e that is selectively engagable by a user to pivot arm portion 16b relative to base portion 18b (e.g., away from base portion 18b or from the closed position to the open position) to enable detent 18d to separate from one of apertures 16d of flexible band 16. Once detent 18d of arm portion 18b is spaced apart from flexible band 16, cinch 18 enables relative sliding movement between flexible band 16 and cinch 18, as indicated by arrows "B" for adjusting a diameter of flexible band 16 and a diameter of opening 12e of bag 12, as indicated by arrows "C". In particular, movement of flexible band 16 in a first direction relative to cinch 18 reduces the diameters of flexible band 16 and opening 12e of bag 12, while movement of flexible band 16 in a second direction (e.g. opposite to the first direction) relative to cinch 18 enlarges the diameters of flexible band 16 and opening 12e of bag 12.

Figure 2:
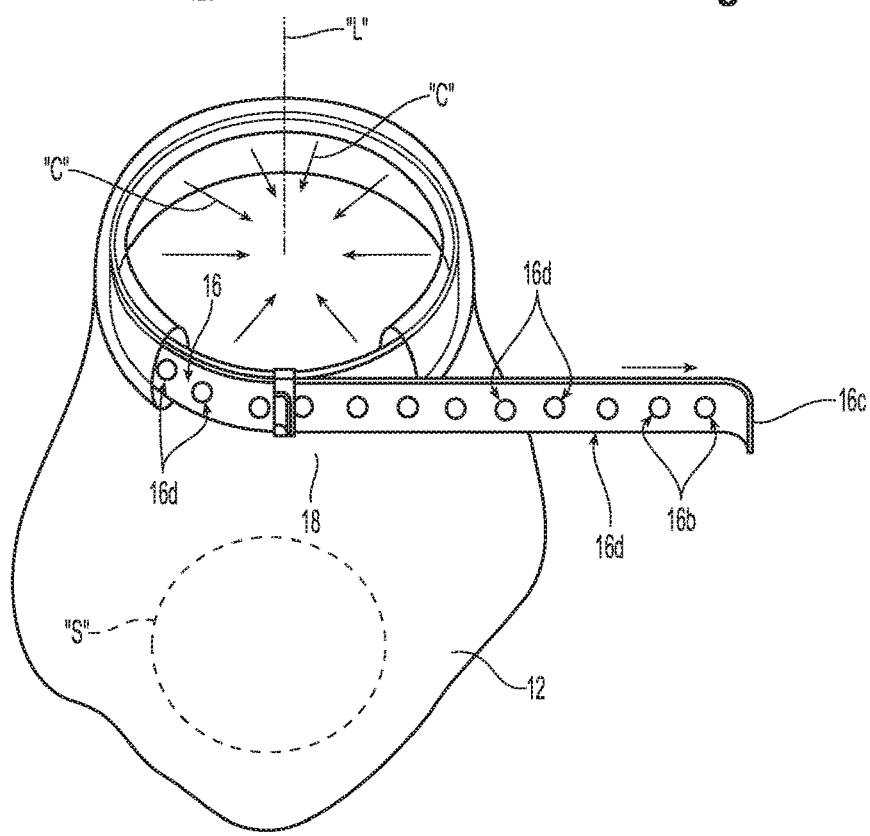
FIG. 2 is a perspective of the specimen retrieval device of FIG. 1 shown in a cinched position.
Figure 3:
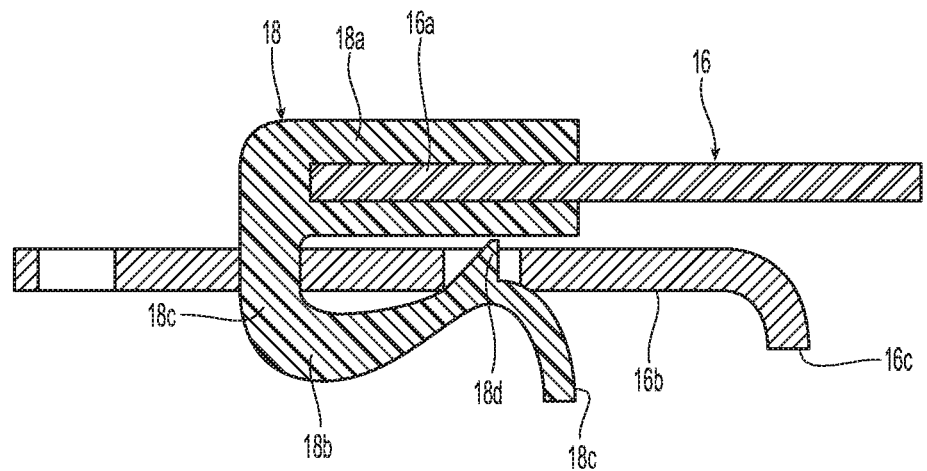
FIG. 3 is an enlarged cross-sectional view of a cinch mechanism of the specimen retrieval device of FIGS. 1 and 2 as taken along section line 3-3 of FIG. 1, the cinch mechanism illustrated in a locked position.

As seen in FIGS. 1 and 2, cinching mechanism 14 of specimen retrieval device 10 enables bag 12 to be selectively moved from an uncinched position (FIG. 1), in which a diameter of opening 12e of bag 12 may be enlarged or at a maximum, to a cinched position (FIG. 2), in which the diameter of opening 12e of bag 12 (or a diameter defined by flexible band 16) is reduced, for instance, to selectively close opening 12e of bag 12. For example, after a specimen "S" is received in bag 12, a clinician can close bag 12 to seal specimen "S" in bag 12 by cinching bag 12 closed with cinching mechanism 14. To close bag 12, release tab 18e of cinch 18 is pressed toward pivot 18c so that arm portion 18b pivots about pivot 18c, as indicated by arrow "A," so that detent 18d of arm portion 18b separates from a first one of apertures 16d of flexible band 16. Second end portion 16b of flexible band 16 can then be drawn in a first direction "B1" relative to cinch 18 so that the diameter of opening 12e of bag 12 is reduced to at least partially close bag 12. When bag 12 is sufficiently closed, the clinician can disengage release tab 18e to enable arm portion 18b, which is configured to bias toward the closed position thereof, to pivot back toward base portion 18a into the closed position thereof so that detent 18d of cinch 18 can be received into a second one of apertures 16d of flexible band 16. As can be appreciated, detent 18d of cinch 18 may be configured to ratchet with respect to apertures 16d. With detent 18d of cinch 18 secured to flexible band 16, flexible band 16 is fixed in place (in a temporary position thereof) to maintain the selected diameter of opening 12e of bag 12 fixed.

To open bag 12, the clinician engages release tab 18e and pivot arm portion 18b away from base portion 18a and out of the second one of apertures 16d. Flexible band 16 may be biased to move in a second direction, as indicated by "B2," relative to cinch 18 to enlarge the diameter of opening 12e of bag 12. For instance, by virtue of shape memory material (e.g., Nitinol) flexible band 16 may spring open (from the temporary position of flexible band 16 towards the initial or permanent position of flexible band 16) so that free end 16c moves toward cinch 18. Additionally or alternatively, flexible band 16 may be drawn, pushed, and/or pulled toward cinch 18 for re-enlarging opening 12e of bag 12.

Cinch mechanism 14 can be adjusted as desired to selectively open and/or close bag 12 to enable opening 12e of bag 12 to have any suitable diameter, for instance, to insert and/or remove specimen "S" therefrom, and/or to close and/or seal specimen "S" therein.

As can be appreciated, bag 12, or portions thereof, may include any suitable polymeric material such as nylon. In some embodiments, bag, or portions thereof, may be transparent or translucent.

Securement of any of the components of the disclosed devices may be effectuated using known securement techniques such welding, crimping, gluing, heat-shrinking, fastening, etc.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, the elements and features shown or described in connection with certain embodiments may be combined with the elements and features of certain other embodiments without departing from the scope of this disclosure, and that such modifications and variations are also included within the scope of this disclosure. Accordingly, the subject matter of this disclosure is not limited by what has been particularly shown and described.

What is claimed is:

1. A specimen retrieval device, comprising:
   a bag having a closed bottom end portion and an open top end portion; and
   a cinch mechanism coupled to the open top end portion, the cinch mechanism including a flexible band secured to the bag and a cinch coupled to the flexible band, the flexible band movable relative to the cinch to reduce or enlarge a diameter of the open top end portion of the bag, the cinch selectively engagable with the flexible band to fix the diameter of the open top end portion of the bag, wherein the cinch includes a base portion and an arm portion, the arm portion pivotally coupled to the base portion between an open position and a closed position.

2. The specimen retrieval device of claim 1, wherein the arm portion is biased toward the closed position.

3. The specimen retrieval device of claim 1, wherein the arm portion includes a detent that contacts the flexible band.

4. The specimen retrieval device of claim 3, wherein the flexible band defines at least one aperture, and wherein the detent is receivable within the at least one aperture to prevent the flexible band from moving relative to the cinch.

5. The specimen retrieval device of claim 1, wherein the flexible band includes a first end portion that is fixedly secured to the cinch and a second end portion that is movable relative to the cinch.

6. The specimen retrieval device of claim 5, wherein the second end portion extends to a free end.

7. The specimen retrieval device of claim 6, wherein the free end includes a hook configuration that prevents the free end from passing through the cinch.

8. The specimen retrieval device of claim 1, wherein the flexible band includes shape memory material.

9. The specimen retrieval device of claim 8, wherein the shape memory material is Nitinol.

10. A cinch mechanism for a specimen retrieval device, the cinch mechanism comprising:
a flexible band; and
a cinch coupled to the flexible band, the flexible band movable relative to the cinch in a first direction to reduce a diameter of a bag of the specimen retrieval device, and in a second direction to enlarge the diameter of the bag, the cinch selectively engagable with the flexible band to prevent the flexible band from moving relative to the cinch, wherein the cinch includes a base portion and an arm portion, the arm portion pivotally coupled to the base portion between an open position and a closed position.

11. The cinch mechanism of claim 10, wherein the arm portion is biased toward the closed position.

12. The cinch mechanism of claim 10, wherein the arm portion includes a detent that contacts the flexible band.

13. The cinch mechanism of claim 12, wherein the flexible band defines at least one aperture, and wherein the detent is receivable within the at least one aperture to prevent the flexible band from moving relative to the cinch.

14. The cinch mechanism of claim 10, wherein the flexible band includes a first end portion that is fixedly secured to the cinch and a second end portion that is movable relative to the cinch.

15. The cinch mechanism of claim 14, wherein the second end portion extends to a free end.

16. The cinch mechanism of claim 15, wherein the free end includes a hook configuration that prevents the free end from passing through the cinch.

17. The specimen retrieval device of claim 10, wherein the flexible band includes Nitinol.

18. A specimen retrieval device, comprising:
a bag having a closed bottom end portion and an open top end portion; and
a cinch mechanism coupled to the open top end portion, the cinch mechanism including a flexible band secured to the bag and a cinch coupled to the flexible band, the flexible band movable relative to the cinch to reduce or enlarge a diameter of the open top end portion of the bag, the cinch selectively engagable with the flexible band to fix the diameter of the open top end portion of the bag, wherein the flexible band includes a first end portion that is fixedly secured to the cinch and a second end portion that is movable relative to the cinch, wherein the second end portion extends to a free end having a hook configuration, the hook configuration prevents the free end from passing through the cinch.

19. A cinch mechanism for a specimen retrieval device, the cinch mechanism comprising:
a flexible band; and
a cinch coupled to the flexible band, the flexible band movable relative to the cinch in a first direction to reduce a diameter of a bag of the specimen retrieval device, and the flexible band movable relative to the cinch in a second direction to enlarge the diameter of the bag of the specimen retrieval device, the cinch selectively engagable with the flexible band to prevent the flexible band from moving relative to the cinch, wherein the flexible band includes a first end portion, the first end portion fixedly secured to the cinch, the flexible band includes a second end portion, the second end portion movable relative to the cinch, and wherein the second end portion of the flexible band extends to a free end having a hook configuration, the hook configuration prevents the free end from passing through the cinch.

* * * * *